(12) United States Patent
Taylor, Jr.

(10) Patent No.: US 7,469,186 B2
(45) Date of Patent: Dec. 23, 2008

(54) FINDING USABLE PORTION OF SIGMOID CURVE

(75) Inventor: Thomas H. Taylor, Jr., Atlanta, GA (US)

(73) Assignee: The United States of America as represented by the Secretary of the Department of Health and Human Services, Centers for Disease Control and Prevention, Washington, DC (US)

(*) Notice: Subject to any disclaimer, the term of this patent is extended or adjusted under 35 U.S.C. 154(b) by 0 days.

(21) Appl. No.: 10/550,377

(22) PCT Filed: Mar. 19, 2004

(86) PCT No.: PCT/US2004/008566

§ 371 (c)(1),
(2), (4) Date: Sep. 20, 2005

(87) PCT Pub. No.: WO2004/084708

PCT Pub. Date: Oct. 7, 2004

(65) Prior Publication Data

US 2006/0265143 A1    Nov. 23, 2006

Related U.S. Application Data

(60) Provisional application No. 60/456,613, filed on Mar. 21, 2003.

(51) Int. Cl.
*G01N 33/48* (2006.01)
*G01N 33/50* (2006.01)
*G06F 19/00* (2006.01)

(52) U.S. Cl. .................................. 702/23; 702/19

(58) Field of Classification Search ............... 702/23, 702/19
See application file for complete search history.

(56) References Cited

U.S. PATENT DOCUMENTS

| | | | |
|---|---|---|---|
| 4,703,017 A | 10/1987 | Campbell et al. | |
| 4,835,099 A | 5/1989 | Mize et al. | |
| 5,616,504 A | 4/1997 | Brown et al. | |
| 5,795,791 A | 8/1998 | Hirai et al. | |
| 5,948,368 A | 9/1999 | Hirai et al. | |
| 6,188,969 B1 | 2/2001 | Minor | |
| 6,277,584 B1 | 8/2001 | Chu et al. | |
| 6,303,305 B1 | 10/2001 | Wittwer et al. | |
| 6,395,480 B1 | 5/2002 | Hefti | |
| 6,403,314 B1 | 6/2002 | Lange et al. | |
| 6,436,721 B1 | 8/2002 | Kuo et al. | |
| 6,440,667 B1 | 8/2002 | Fodor et al. | |
| 6,503,720 B2 * | 1/2003 | Wittwer et al. ............... | 435/6 |

(Continued)

OTHER PUBLICATIONS

Becking, L.G.M.Baas, "On the Analysis of Sigmoid Curves". Mar. 1946, Acta Biotheoretica, vol. 8, Nos. 1-2, pp. 42-59.*

(Continued)

*Primary Examiner*—Eliseo Ramos Feliciano
*Assistant Examiner*—Janet L Suglo
(74) *Attorney, Agent, or Firm*—Klarquist Sparkman, LLP

(57) ABSTRACT

Various technologies are described by which the usable portion or threshold value of a sigmoid curve is found. Such techniques can be useful, for example, when determining the concentration or presence of a substance in a test sample. Various techniques can avoid variability in results.

30 Claims, 16 Drawing Sheets

U.S. PATENT DOCUMENTS

| | | | |
|---|---|---|---|
| 6,514,770 | B1 | 2/2003 | Sorin |
| 6,887,710 | B2 | 5/2005 | Call et al. |
| 7,373,253 | B2 * | 5/2008 | Eyre .......................... 702/19 |
| 2002/0034732 | A1 | 3/2002 | Capon et al. |
| 2002/0082386 | A1 | 6/2002 | Mangold et al. |
| 2002/0160012 | A1 * | 10/2002 | Kaastrup ................. 424/185.1 |
| 2003/0157498 | A1 | 8/2003 | Eyre et al. |

OTHER PUBLICATIONS

"DeCypher Introduction, The Complete Solution for Accelerated Biocomputing," TimeLogic Corporation, http://www.timelogic.com/decypher_intyo.html, 3 pages, website visited on Oct. 22, 2002.

"ELISA Activity—ELISA data from three patients," *The Biology Project—Immunology*, The University of Arizona, http://www.biology.arizona.edu/immunology/activities/elisa/elisa1.html, 1 page, website visited Oct. 22, 2002.

"ELISA Activity—False Positives," *The Biology Project—Immunology*, The University of Arizona, http://www.biology.arizona.edu/immunology/activities/elisa/false.html, 1 page, website visited Oct. 22, 2002.

"ELISA Activity—The ELISA Method," *The Biology Project—Immunology*, The University of Arizona, http://www.biology.arizona.edu/immunology/activities/elisa/technique.html, 1 page, website visited Oct. 22, 2002.

"ELISA Activity—The ELISA," *The Biology Project—Immunology*, The University of Arizona, http://www.biology.arizona.edu/immunology/activities/elisa/elisa_intro.html, 1 page, website visited Oct. 22, 2002.

"Enhancing Human Health Through Better Decisions—from Discovery Through Development to Commercialization—and Beyond," SAS Institute Inc., 2 pages, http://www.sas.com/industry/pharma/index.html, website visited on Oct. 22, 2002.

"Enzyme-Linked Immunosorbent Assay," *Emerging Infectious Diseases*, vol. 8, No. 10. CDC, 3 pages, 2002.

"General Policy Issues," *WHO Drug Information*, vol. 14, No. 1, pp. 1-38, 2000.

"PROC NLIN Statement," SAS Institute Inc., 5 pages, http://www.id.unizh.ch/software/unix/statmath/sas/sasdoc/stat/chap45/sect4.htm, Copyright 1999.

"Product Information: Prospect Pro: PROtein Structure Prediction and Evaluation Computer Toolkit," Bioinformatics Solutions Inc., 2 pages, http://www.bioinformaticssolutions.com/products/prospect.php, website visited Oct. 22, 2002.

"StatLIA Main Page: StatLIA Software," Brendan Scientific Corporation, 3 pages, http://www.brendan.com/sl_main.htm, website visited on Oct. 22, 2002.

"Using the ELISA Assay for Disease Detection—Student Handout," The University of Arizona, Biotech Project, http://biotech.biology.arizona.edu/labs/ELISA_assay_students.html, 4 pages, website visited Oct. 22, 2002.

"Worldwide Cellular Assays Market Expected to Reach $500 Million on 2007," Front Line Strategic Consulting Inc., http://www.theinfoshop.com/press/fe10229_en.shtml, 2 pages, website visited on Oct. 22, 2002.

"Zeus Scientific, Inc.—Technical Topics & Algorithms," Zeus Scientific, Inc., 1 page, http://www.zeusssci.com/tech.html, website visited on Oct. 22, 2002.

Costa, "CDC Set To Begin Wide-Reaching Anthrax Vaccine Studies This Month," *Inside The Pentagon*, http://www.marjorbates.com/news/08mar01_itp.htm, 7 pages, Mar. 8, 2001.

Guarino et al., "A High Throughput, Cell-Based Assay for Metabolic Toxicity," http://www.bdbiosciences.com/discovery_labware/Products/drug_discovery/polystyrene_microplates/oxygen_biosensor_system/pdf/O2_Metabotox-GordonConf.pdf, 1 page, GenTest Corporation, website visited Jan. 10, 2003.

Henderson, "Chapter 5: Affinity Separations" in Combined Microfiltration and Membrane-Based Affinity Separation Thesis, pp. 108-121, http://website.lineone.net/~jim.henderson/work/dphil.html, 1999.

Marshall et al., "Lack of Autoantibody Production Associated with Cytomegalovirus," *Arthritis Res*, 4:R6, http://arthritis-research.com/4/5/R6, 5 pages, 2002.

O'Connell, et al., "Calibration and Assay Development Using the Four-Parameter Logistic Model," *Chemometrics and Intelligent Laboratory Systems*, vol. 20, Issue 2, Elsevier Science B.V., pp. 97-200, Sep. 1993.

Peterson, "Chapter 6 Data Fitting," in *Numerical Analysis: Adventures in Frustration*, 15 pages, http://www.ces.clemson.edu/~petersj/Agents/MatLabNA/MatLabNA006.html, website visited Mar. 12, 2003.

Phizicky et al., "Protein-Protein Interactions: Methods for Detection and Analysis," *Microbiological Reviews*, vol. 59, No. 1, pp. 94-123, Mar. 1995.

Quinn et al., "Specific, Sensitive, and Quantitative Enzyme-Linked Immunosorbent Assay for Human Immunoglobin G Antibodies to Anthrax Toxin Protective Antigen," *Bioterrorism-Related Anthrax*, vol. 8, No. 10, 15 pages, http://www.cdc.gov/ncidod/EID/vol8no10/02-0380.htm, Oct. 2002.

Quinn et al., "Specific, Sensitive, and Quantitative Enzyme-Linked Immunosorbent Assay for Human Immunoglobulin G Antibodies to Anthrax Toxin Protective Antigen," *Bioterrorism-Related Anthrax*, vol. 8, No. 10, 3 pages, http://www.cdc.gov/ncidod/EID/vol8no10/02-0380-G1.htm, Oct. 2002.

Strandh, "Insights Into Weak and Affinity Antibody-Antigen Interactions: Studies and Affinity Chromatography and Optical Biosensor," Printed in Sweden at the University of Kalmar, 59 pages, 2000.

Yuancai et al., "Remarks on Height-Diameter Modeling," United States Department of Agriculture, Research Note SRS-IO, 8 pages, Nov. 2001.

Examination Report, Australian Government—IP Australia, from counterpart Australian Application No. 2004224317, Jan. 21, 2008, 3 pages.

Taylor et al., "Novel Mathematical approach to TNA endpoints," 5th Intl. Conf. Anthrax, 3rd Int. Workshop Mol. Biol. *Bacillus cereus B. anthracis B. thuringiensis*, Mar. 30, 2003-Apr. 4, 2003, 3 pages.

Taylor et al., "Novel Mathematical approach to TNA endpoints (Poster)," 5th Intl. Conf. Anthrax, 3rd Int. Workshop Mol. Biol. *Bacillus cereus B. anthracis B. thuringiensis*, Mar. 30, 2003-Apr. 4, 2003, 1 page.

* cited by examiner

ANALYSIS RESULTS

| SAMPLE | CONC. | PRESENT? | OBS. | DISCARDS |
|--------|-------|----------|------|----------|
| 00452  | .452  | YES      | 6    | 2        |
| 00459  | .780  | YES      | 5    | 0        |
| 00486  | .450  | YES      | 6    | 4        |
| 00708  | ???   | YES      | 4    | 4        |
| 00710  | ???   | NO       | 4    | 4        |
| 00740  | .020  | YES      | 5    | 1        |

TNA PLATE: NHP81A, READ ON [DATE]                                265
WARNING: RESULTS MAY BE UNRELIABLE FOR PARTIAL CURVES AND/OR IF ED50 < INITIAL DILUTION

SOURCE=NHP81A STD=AVR731 STD ED50=1211 COMPUTATION METHOD=GAUSS ANALYST=HL READDATE=[DATE]

| SAMNO | SAMPLE | CURVE FIT STATUS | INITIAL DILUTION | FLAGNADA | FLAG34 | FLAG ED50 OF STD | RSQRD | FLAGRSQRD |
|---|---|---|---|---|---|---|---|---|
| 1 | 12275434 | CONVERGED | 200 | | | | 0.985 | |
| 2 | 12292526 | CONVERGED | 100 | | | | 0.982 | |
| 3 | 12294626 | CONVERGED | 200 | | | | 0.989 | |
| 4 | AVR731 | CONVERGED | 200 | | OK | ?? | 0.997 | |

WARNING:

| SAMNO | LOW TITER ED50 | QUANTIF. TITER | THRESHOLD TITER | NF50 | OD RANGE OF STD | MEAN OD OF POS. CNTRL. | STD DEV OD OF POS. CNTRL. |
|---|---|---|---|---|---|---|---|
| 1 | 1299 | 1740 | 2220 | 1.07 | . | 1.01 | 0.037 |
| 2 | 870 | 1180 | 1560 | 0.72 | . | 1.14 | 0.095 |
| 3 | 1414 | 1890 | 2450 | 1.17 | . | 1.04 | 0.029 |
| 4 | 1211 | 1810 | 2550 | 1.00 | 0.73 | 0.94 | 0.015 |

| SAMNO | CV OF OD OF POS. CNTRL. | DELTA: BOT. OD TRIPLICATE & NEG. CNTRL. | MEAN OD OF NEG. CNTRL. | STD DEV OD OF NEG. CNTRL. | CV OF OD OF NEG. CNTRL. | UPPER ASYMP. | LOWER ASYMP. | MAXIMUM OD TRIPLE |
|---|---|---|---|---|---|---|---|---|
| 1 | 4% | 0.00 | 0.28 | 0.002 | 1% | 0.98 | 0.29 | 1.08 |
| 2 | 8% | 0.01 | 0.28 | 0.002 | 1% | 0.98 | 0.28 | 1.09 |
| 3 | 3% | 0.01 | 0.28 | 0.002 | 1% | 0.98 | 0.28 | 1.07 |
| 4 | 2% | 0.01 | 0.28 | 0.002 | 1% | 0.98 | 0.27 | 0.99 |

| SAMNO | LOWEST OD TRIPLE | MAXIMUM CV OF ODS | POINTS-BASED IGG CONC. | CURVE-BASED IGG CONC. | VERSION | QCCHECK |
|---|---|---|---|---|---|---|
| 1 | 0.28 | 4% | 260.3 | 190.6 | ED50.45CORE01 | |
| 2 | 0.27 | 6% | 136.7 | 126.6 | ED50.45CORE01 | |
| 3 | 0.27 | 3% | 233.6 | 204.8 | ED50.45CORE01 | |
| 4 | 0.27 | 3% | 177.3 | 171.9 | ED50.45CORE01 | ?? |

1600

FINDING USABLE PORTION OF SIGMOID CURVE

CROSS REFERENCE TO RELATED APPLICATIONS

This is the U.S. National Stage of International Application No. PCT/US2004/008566, filed Mar. 19, 2004, which was published in English under PCT Article 21(2), which in turn claims the benefit of U.S. Provisional Application No. 60/456,613 filed Mar. 21, 2003. Both applications are incorporated herein in their entirety.

TECHNICAL FIELD

The technical field relates to analyzing observations of a sample to determine the concentration of a substance within the sample, and more particularly to determining a concentration via a sigmoid curve representing observations for the sample.

BACKGROUND

One way of determining the concentration of a substance in a sample is by performing serial dilution on the sample. Serial dilution techniques collect a finite number of data points for the sample by taking one or more observations (e.g., indicating optical density) of various dilutions (e.g., dilutions formed by adding various quantity of diluent to the sample). For example, dilutions of 10%, 1%, 0.1%, etc. can be measured for optical density.

The results can then be used to determine a concentration of the substance in the sample via reference to a sigmoid curve representing serial-dilution observations for a sample having a known concentration of the substance (sometimes called a "standard" or "characteristic" sigmoid curve). FIG. 1 shows such a sigmoid curve 120. The sigmoid curve can be represented by the four-parameter Formula (1).

$$f(x) = \beta_2 + \frac{\beta_1 - \beta_2}{1 + \left(\frac{x}{\beta_3}\right)^{\beta_4}} \quad (1)$$

The parameters of Formula (1) can be chosen so that the function $f(x)$ calculates the optical density based on a particular dilution x. Given an optical density 130 for a sample having an unknown concentration of the substance and the degree of dilution associated with the sample, the concentration of the substance can be back-calculated. In practice, plural observations of the optical density can be taken for plural degrees of dilution and applied to the standard curve.

Various techniques have been used to define the curve, analyze the observations, and calculate a concentration. One method is described by O'Connell, et al., "Calibration and assay development using the four-parameter logistic model," *Chemometrics and Intelligent Laboratory Systems*, 20 (1993) 97-114, Elsevier Science Publishers B.V., Amsterdam ("O'Connell"), which is hereby incorporated herein by reference. The O'Connell approach describes determining a minimum detectable concentration (MDC) and a reliable detection limit (RDL).

The O'Connell technique can produce significant variability in its results. In certain scenarios, variability is to be avoided. Therefore, there exists a need for technologies that avoid variability in their results and otherwise make better use of the sigmoid curve.

SUMMARY

Various technologies described herein proceed by analyzing data via a sigmoid curve, such as a standard sigmoid curve representing observations of a sample having a known quantity of a substance.

Observation of a test sample can be taken (e.g., in serial dilution scenarios) for a sample, and the technologies described herein can be applied when calculating concentration of a substance within the sample via the sigmoid curve.

In some examples, derivative techniques are applied to determine various points or ranges of the curve. The points or ranges can represent the usable portion of the sigmoid curve or a threshold value reliably indicating presence of the substance.

Some of the technologies exhibit superior reduction in variability of results and are thus useful in a variety of fields, such as testing for levels of antibodies or antigens in a sample. For example, the technologies can be used when testing for titers of antibodies or antigens (e.g., in serum) via serial dilution. The technologies can also be applied with advantage to a variety of scenarios, such as bioassay, polymerase chain reactive ("PCR") assay, radioimmuno assay ("RIA"), cell growth assay, cell death assay, enzyme-linked immunosorbent assay ("ELISA"), toxin neutralization assay ("TNA") (e.g., scenarios involving determining the concentration of biological toxins such as anthrax), and flow cytometry scenarios, or any test in which sample results are derived from a standard sigmoid curve.

Additional features and advantages of the disclosed technologies will be made apparent from the following detailed description of illustrated embodiments, which proceeds with reference to the accompanying drawings.

BRIEF DESCRIPTION OF THE DRAWINGS

FIG. 12 is a screen shot of an exemplary user interface for presenting results of the technologies described herein.

FIGS. 15 and 16 are a screen shot of an exemplary user interface for presenting results of the technologies in text form.

DETAILED DESCRIPTION

EXAMPLE 1

Exemplary Overview

Figure 1:
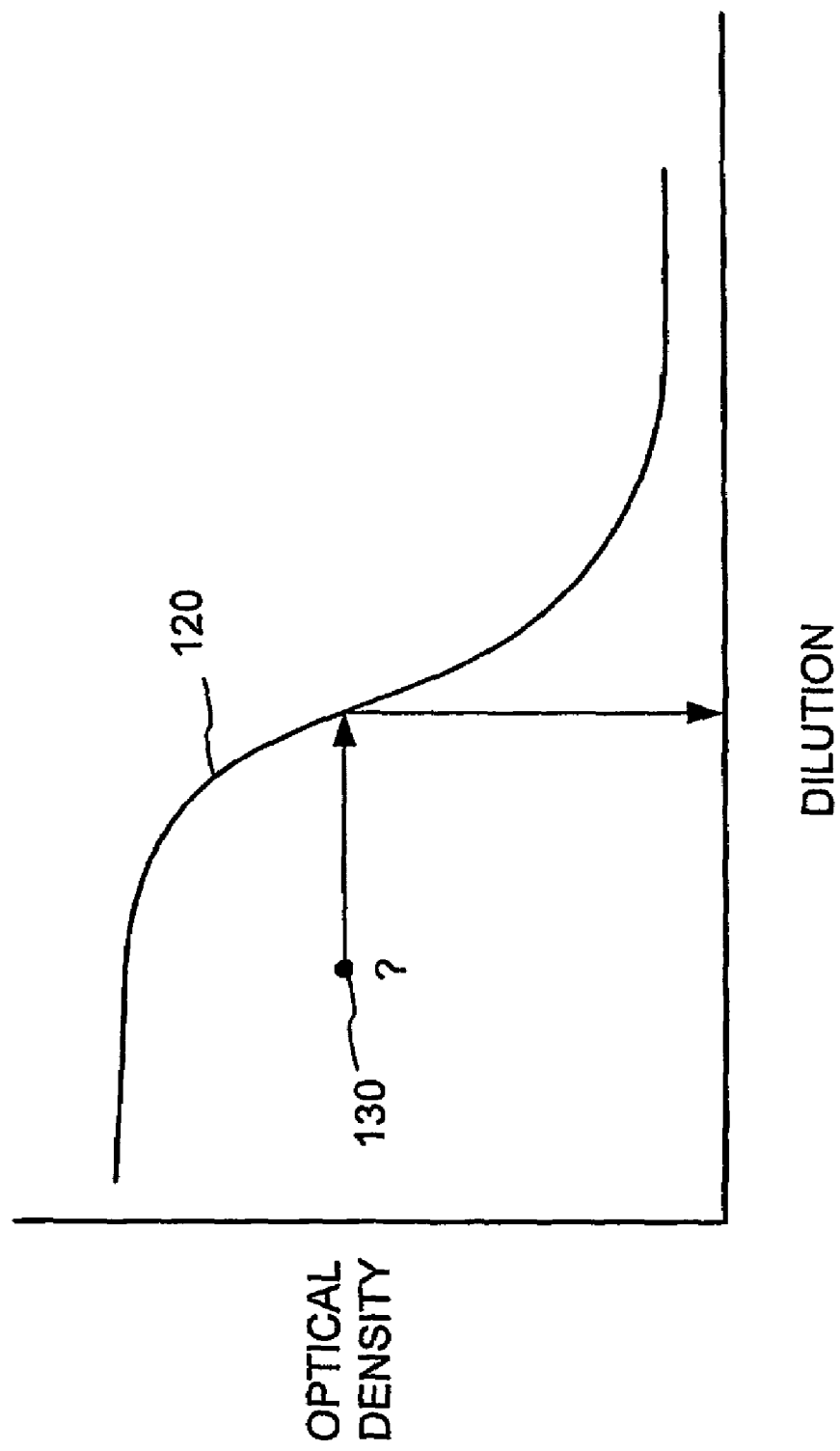
FIG. 1 shows an exemplary sigmoid curve.
Figure 2:
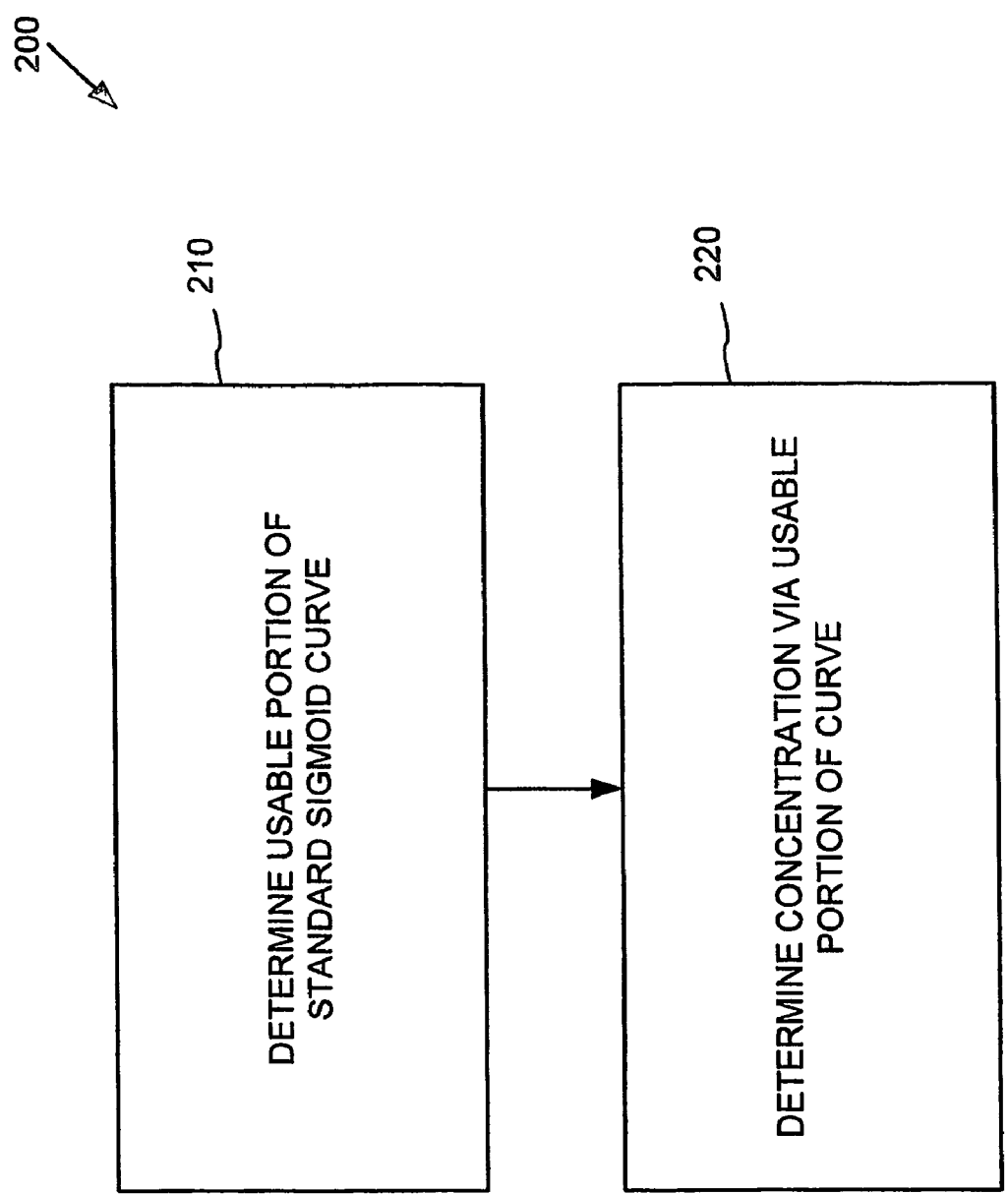
FIG. 2 is a flowchart of an exemplary method for determining concentration in a test sample via a sigmoid curve.

In various of the examples described herein, calculations for determining concentration of a substance in a test sample are performed by identifying a usable portion of a sigmoid curve. Performing the calculations with the usable portion of the curve can improve or optimize the concentration calculation. The portion of the curve that is usable can be determined via derivatives. FIG. 2 shows an exemplary method 200 for determining the concentration of a substance in a test sample via a sigmoid curve. The method 200 can be implemented in software.

At 210, the usable portion of a standard sigmoid curve is determined. For example, a range of points between two endpoints can be defined as the usable portion. The standard sigmoid curve can be generated via observations of a sample having a known amount of the concentration present Observations can be taken for different dilutions (e.g., dilution ratios). In practice, plural observations can be taken for each dilution. To facilitate calculations related to the curve, a curve represented via four parameters (e.g., such as those of Formula 1) can be fit to the observations.

At 220, the concentration (e.g., amount or quantity) of a substance in a test sample can be determined via the usable portion of the curve. For example, given a set of observations of the test sample, some of the observations may relate to portions of the curve outside of the usable area. Such observations need not be included in concentration calculation. Instead, a subset of the observations (e.g., those associated with the usable portion of the curve) can be used in the calculations to determine concentration.

EXAMPLE 2

Exemplary Determination of Usable Portion

Figure 3:
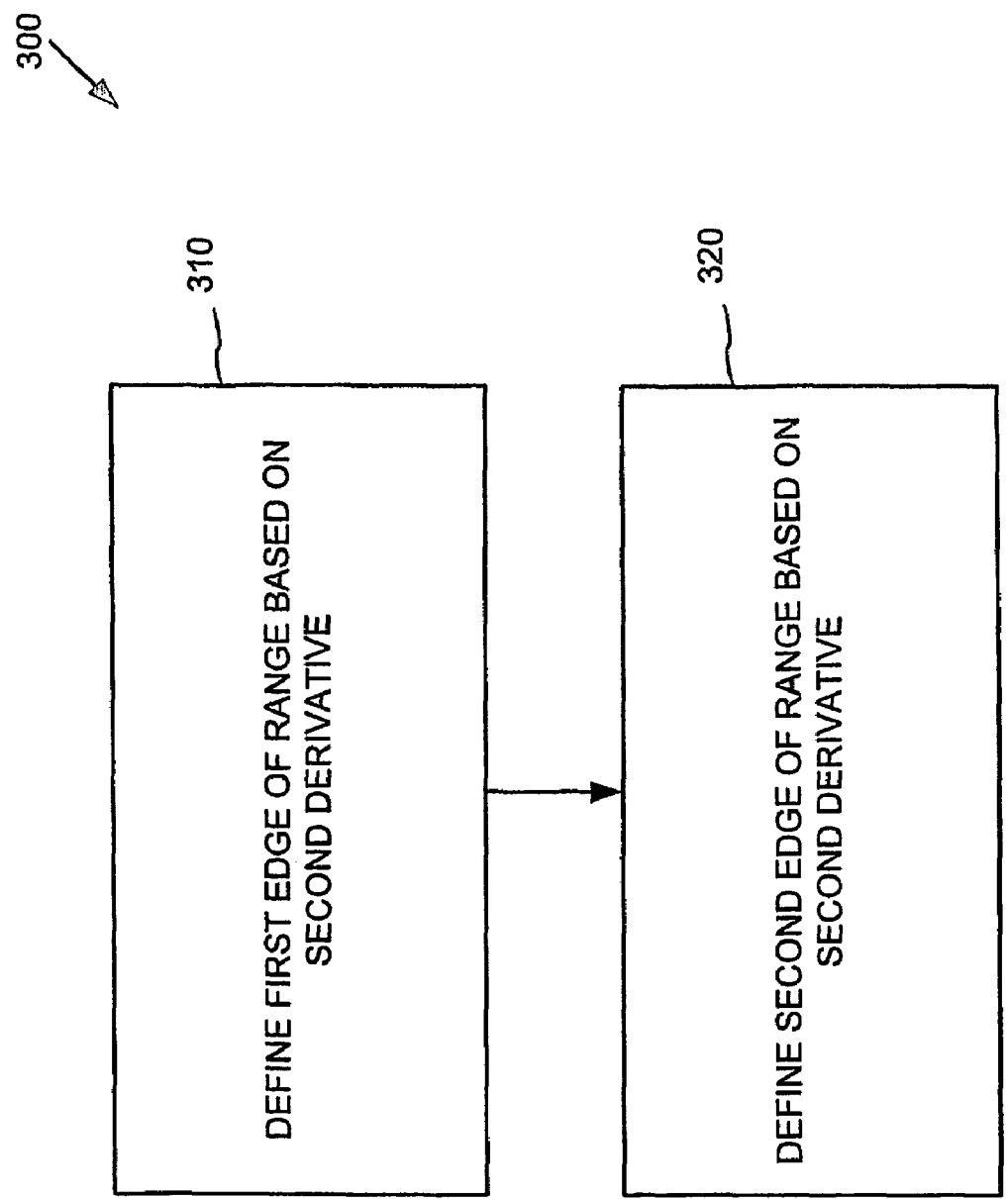
FIG. 3 is a flowchart of an exemplary method for determining the usable portion of a sigmoid curve.

The usable portion of a sigmoid curve (e.g., a standard sigmoid curve), can be determined via derivatives of the sigmoid curve. For example, a maximum and minimum of the second derivative can be used. FIG. 3 shows an exemplary method 300 by which the usable portion of a sigmoid curve can be determined. The method 300 can be implemented in software.

At 310, a first bound (e.g, endpoint) of the range is found via the second derivative of the sigmoid curve (e.g., by finding a local minimum or local maximum of the second derivative of a representation of the curve, such as the four-parameter logistic function). At 320, the other bound (e.g., endpoint) of the range is found via the second derivative of the sigmoid curve (e.g., by finding a local maximum or local maximum, inflection of the second derivative of a representation of the curve, such as the four-parameter logistic function).

The usable portion, then, can be determined as the portion of the sigmoid curve between the two bounds (e.g., endpoints).

EXAMPLE 3

Exemplary Implementation of Determination of Usable Portion

Figure 4:
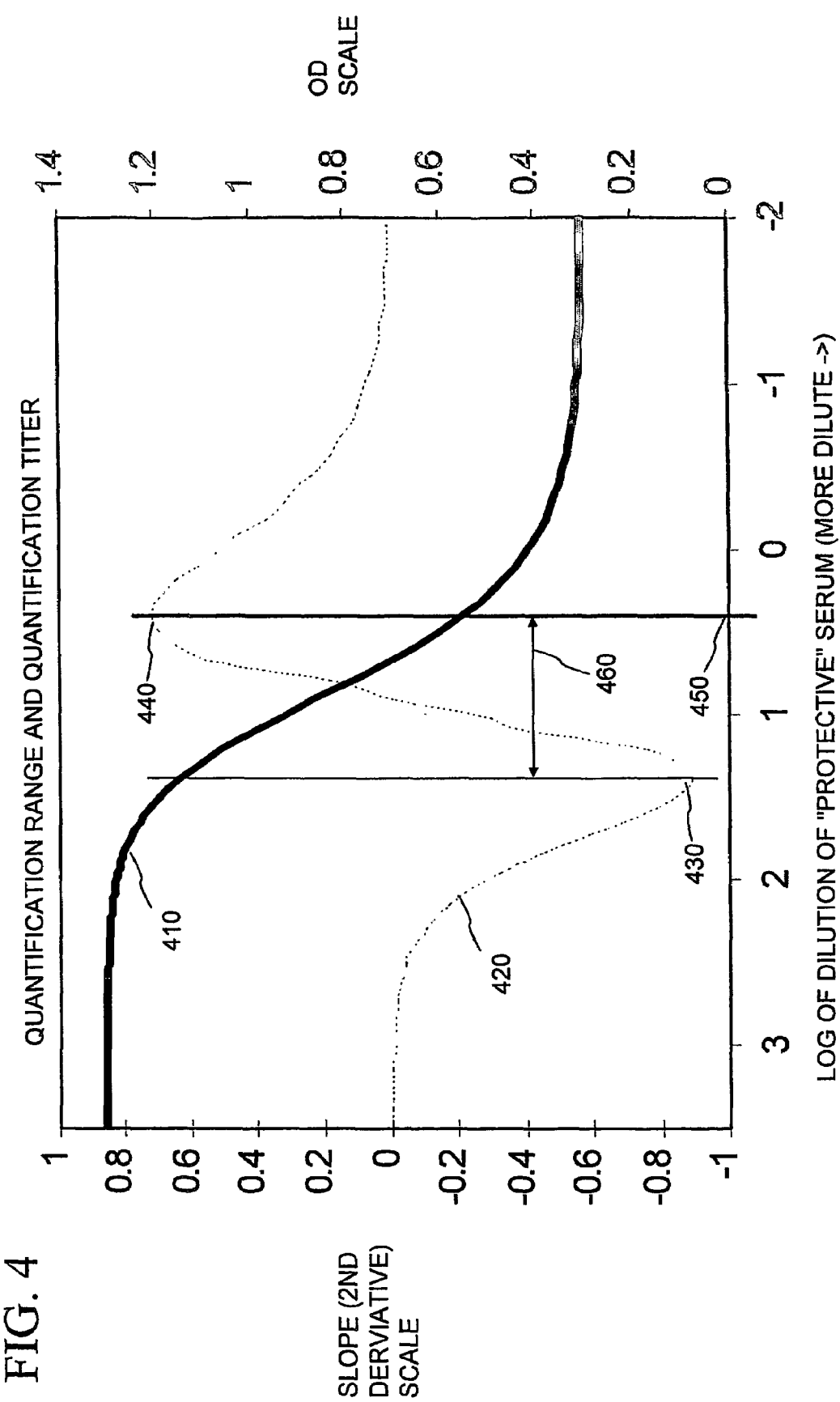
FIG. 4 shows an exemplary implementation of a method for determining the usable portion of a sigmoid curve, such as the method shown in FIG. 3.

FIG. 4 shows an exemplary implementation of determining a usable portion of a sigmoid curve, such as the method 300 shown in FIG. 3. In the example, a standard sigmoid curve 410 has been generated by finding appropriate parameters for Formula (1). Such an approach is sometimes called "fitting a curve to the data." A second derivative 420 of the curve 410 is also shown.

A first point 430 on the second derivative 420 indicates a point on the curve 410 designated as a bound (e.g., a minimum of the second derivative 420 in the example). A second point 440 on the second derivative 430 indicates another point on the curve 410 designated as a bound (e.g., a maximum of the second derivative 420 in the example).

The range 460 of the curve 410 between the two bounds 430, 440 is sometimes called the "quantification range" because it is the range of the curve that is considered usable when determining the concentration of a substance in a test sample.

The point value 450 associated with the point 440 is sometimes called the "quantification titer" because it indicates a value beyond which the curve 440 is no longer useful (e.g., a lower bound of concentration reliably calculable via the curve).

EXAMPLE 4

Exemplary Determination of a Threshold Value for Sigmoid Curve

A threshold value useful in calculating concentration of a substance in a test sample can be determined in a variety of ways. One way involves finding a threshold value at which a first derivative for the curve reaches a benchmark value. Such a benchmark value can be empirically determined (e.g., chosen by a researcher based on evaluation of a number of standard sigmoid curves) and then used uniformly throughout In one implementation, the benchmark value is designated as thirty percent (30%) of the maximum of the first derivative; however, a value approximating thirty percent or a different value may be useful in other scenarios. Any of the methods can be implemented in software.

The point at which the first derivative is equal to the threshold is sometimes called the "threshold titer" because it indicates a minimum detectable concentration according to the technique. Thus, if an observation of a test sample indicates a value above the threshold titer, presence of the substance is indicated, even if the exact concentration may not be reliably determined. Under some scenarios (e.g., detection of toxins), such a threshold titer can be used to advantage.

Figure 5:
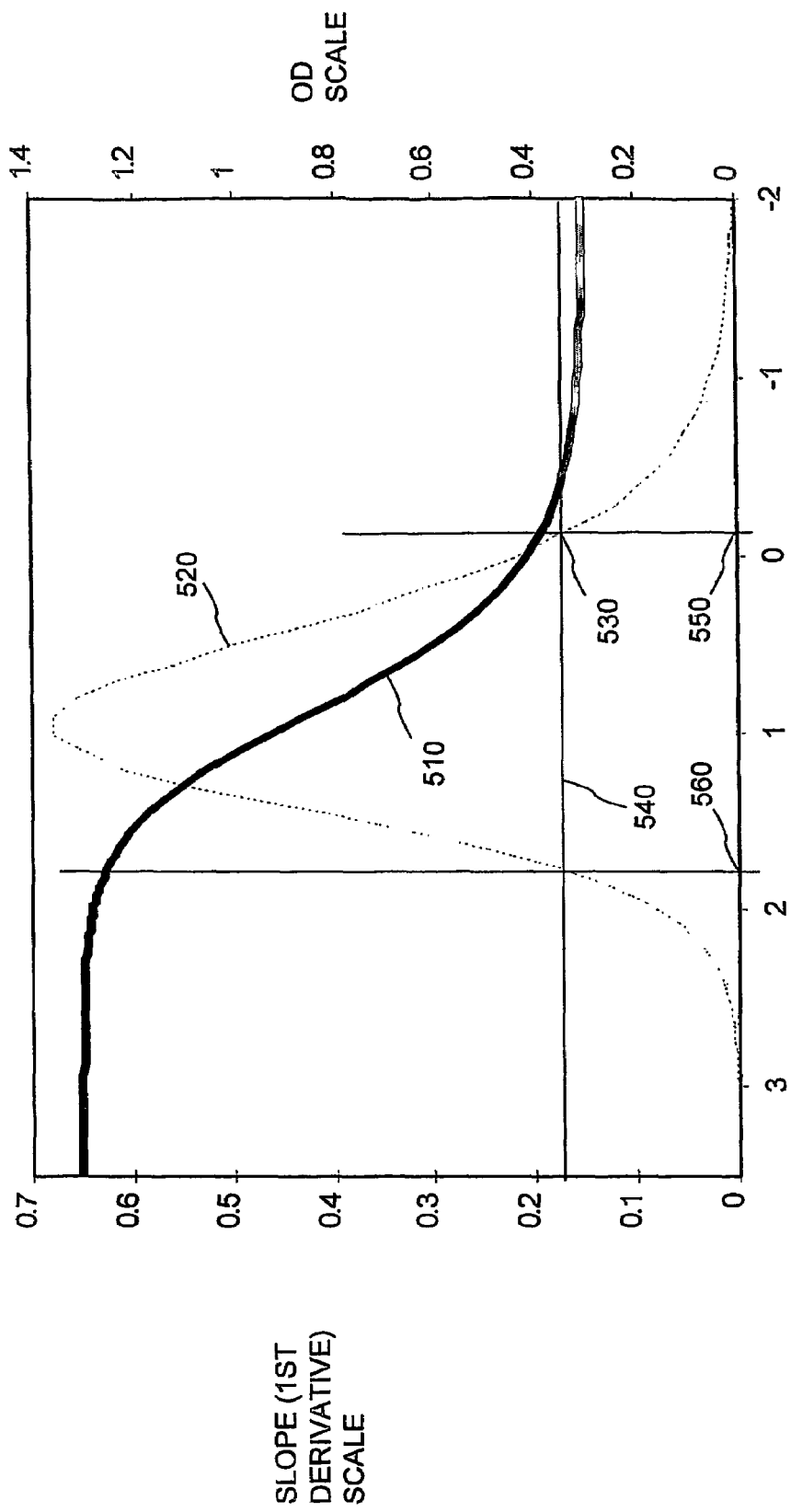
FIG. 5 shows an exemplary implementation of a method for determining a threshold titer on a sigmoid curve.

FIG. 5 shows an exemplary implementation of a method for finding a threshold titer 550 via a first derivative 520 of the related standard sigmoid curve 510. The example portrays a scenario involving measurements of optical density ("OD") for various dilutions of a test sample, but can be applied to other scenarios involving measuring concentration for a test sample.

In the example, a benchmark value 540 is used to determine a point 530 on the first derivative 520 at which the standard curve 510 crosses the benchmark value 540. From the point 530, a threshold titer value 550 can be determined. If a sample has an observation above the threshold titer value 550, presence of the substance being measured is indicated.

In the example, the first derivative 520 has two points at which the curve 510 crosses the benchmark value 540. The point related to the lowest concentration (e.g., the lower value of the curve 510) is used.

The threshold titer value 550 can be used in a method to determine whether the substance of interest is present. For example, a sample for which at least one observation indicates at least such a value can be designated as containing the substance of interest Although the example describes a threshold titer, the technology can be applied to metrics other than titers.

If desired, another threshold at 560 can be found via the first derivative and used in certain scenarios.

Example 5

Exemplary Method Using Derivatives to Determine Concentration

Figure 6:
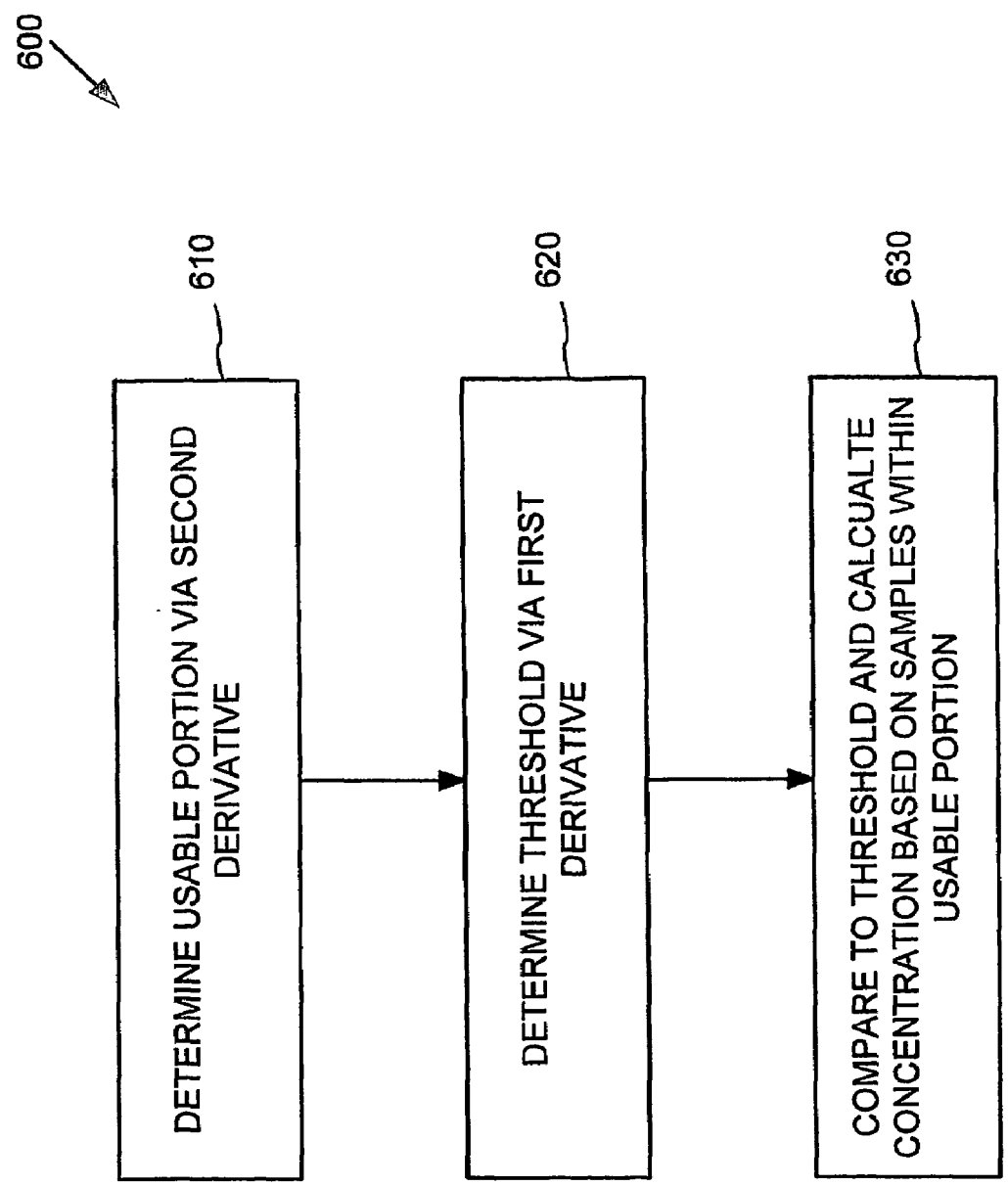
FIG. 6 is a flowchart of an exemplary method for using derivatives to determine the concentration of a substance in a test sample.

FIG. 6 shows an exemplary method 600 using derivatives to determine substance concentration for a test sample. The method 600 can be implemented in software.

At 610, a usable portion of a sigmoid curve is determined (e.g., via any of the technologies described herein).

At 620, a threshold value (e.g., threshold titer) is determined (e.g., via any of the technologies described herein).

At 630, for one or more observations of a sample having unknown substance concentration, the observations are compared to the threshold and a concentration is calculated for them via the usable portion of the curve. Those observations associated with a non-usable portion of the curve are not included. However, an observation above the threshold can indicate presence of the substance, even if a concentration cannot be calculated for the observation.

In practice, 610 and 620 may be performed once for a standard curve, and 630 may be performed plural times for plural samples (e.g., at a different time, location, or by a different computer user at a different computer). Alternatively, in other scenarios, 610 and 620 may be performed plural times for the standard curve (e.g., if the standard test serum is included plural times on plural respective plates).

Example 6

Exemplary Illustration of Back-Calculation Via Sigmoid Curve

Figure 7:
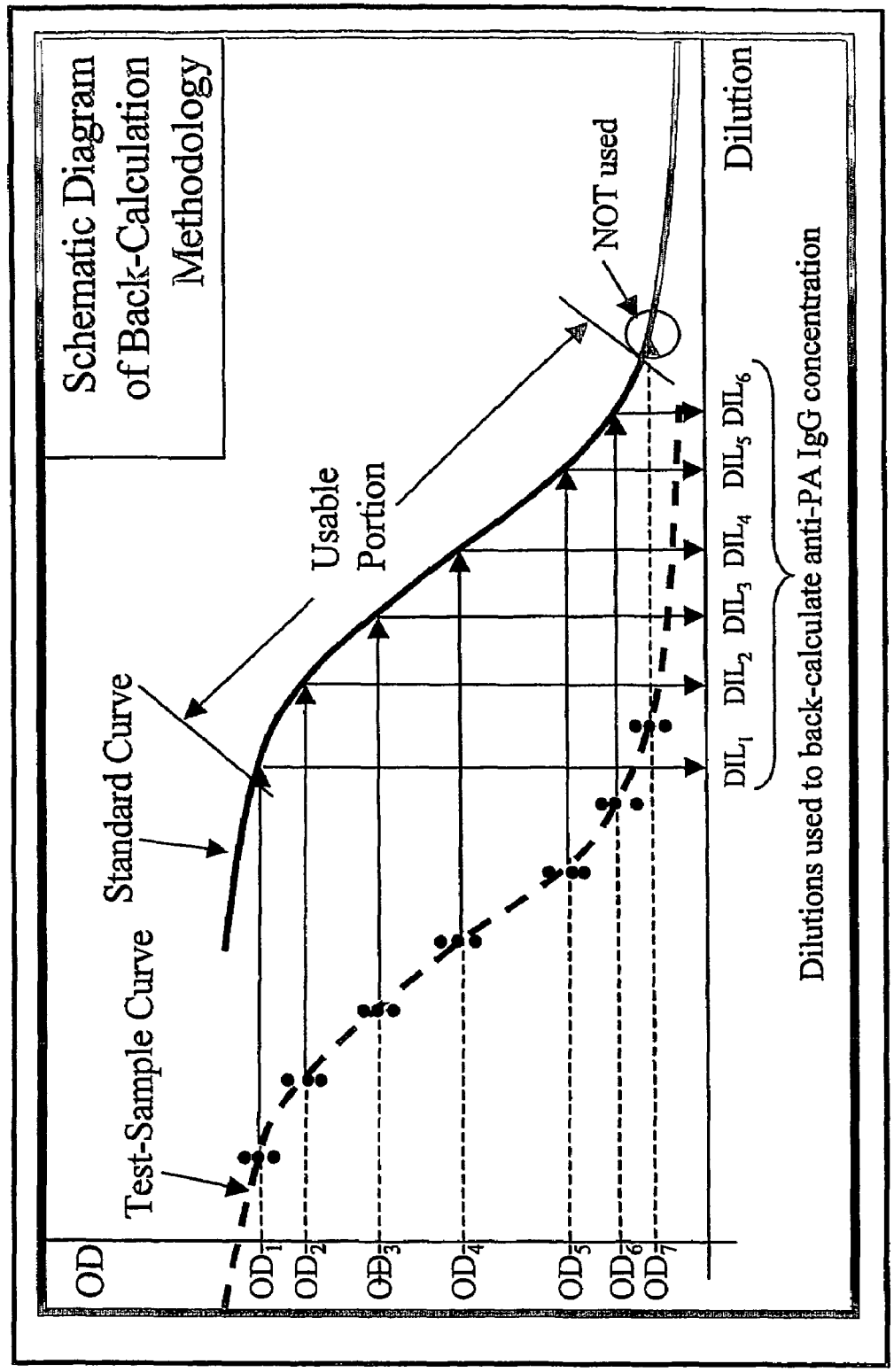
FIG. 7 shows an exemplary sigmoid curve employed in a back calculation technique.
Figure 8:
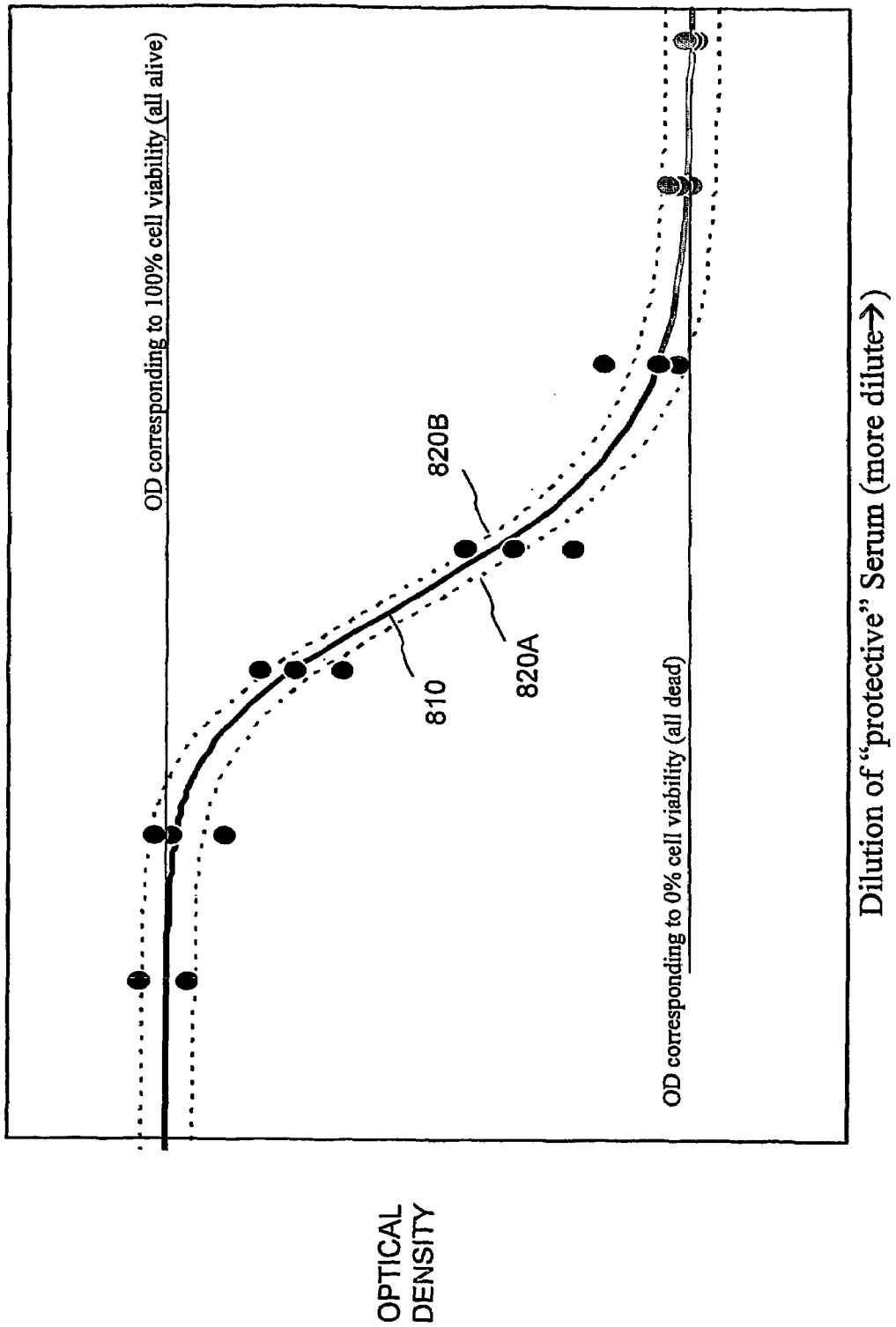
FIG. 8 shows an exemplary sigmoid curve fit to data.
Figure 9:
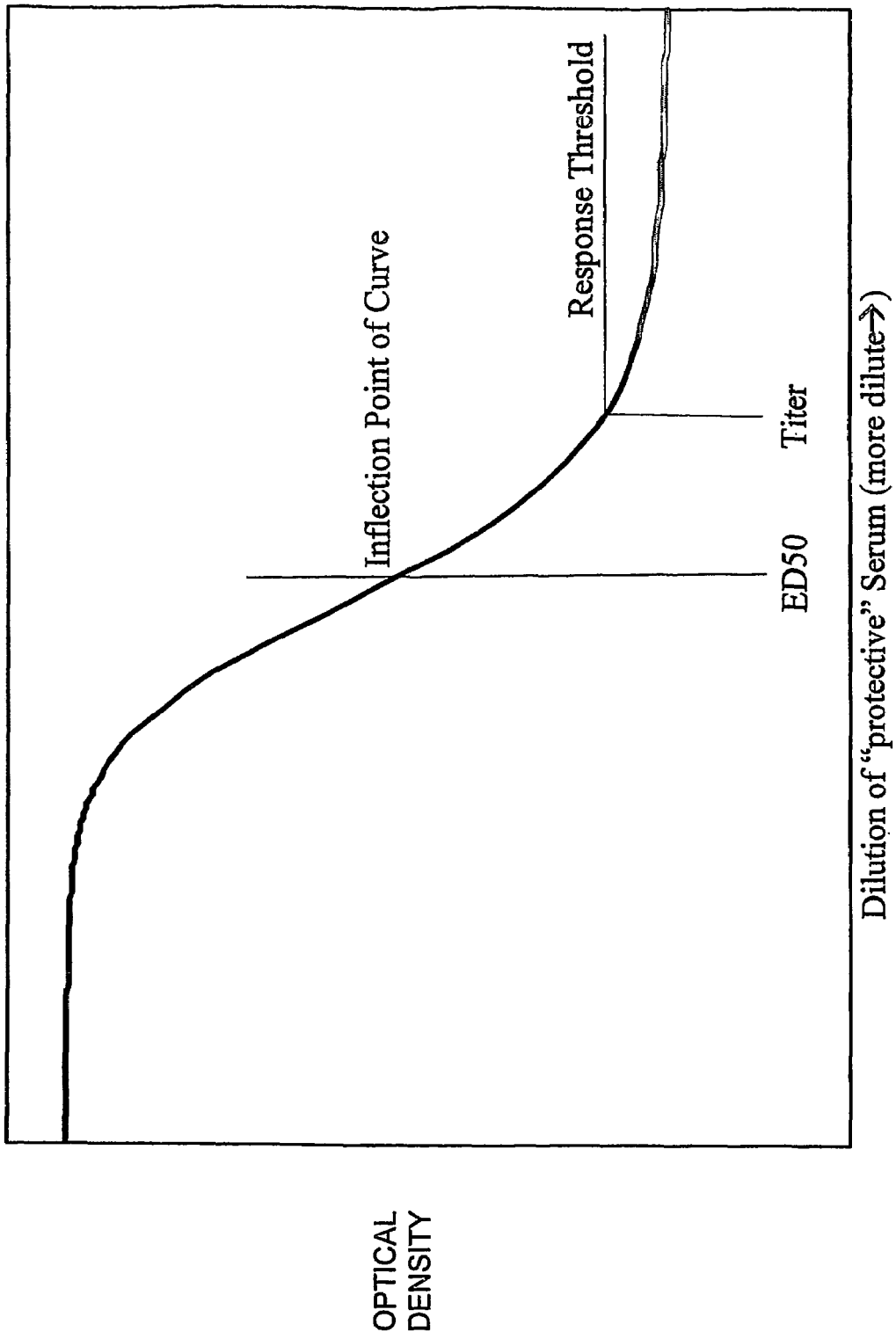
FIG. 9 shows an exemplary curve showing titer computation.
Figure 10:
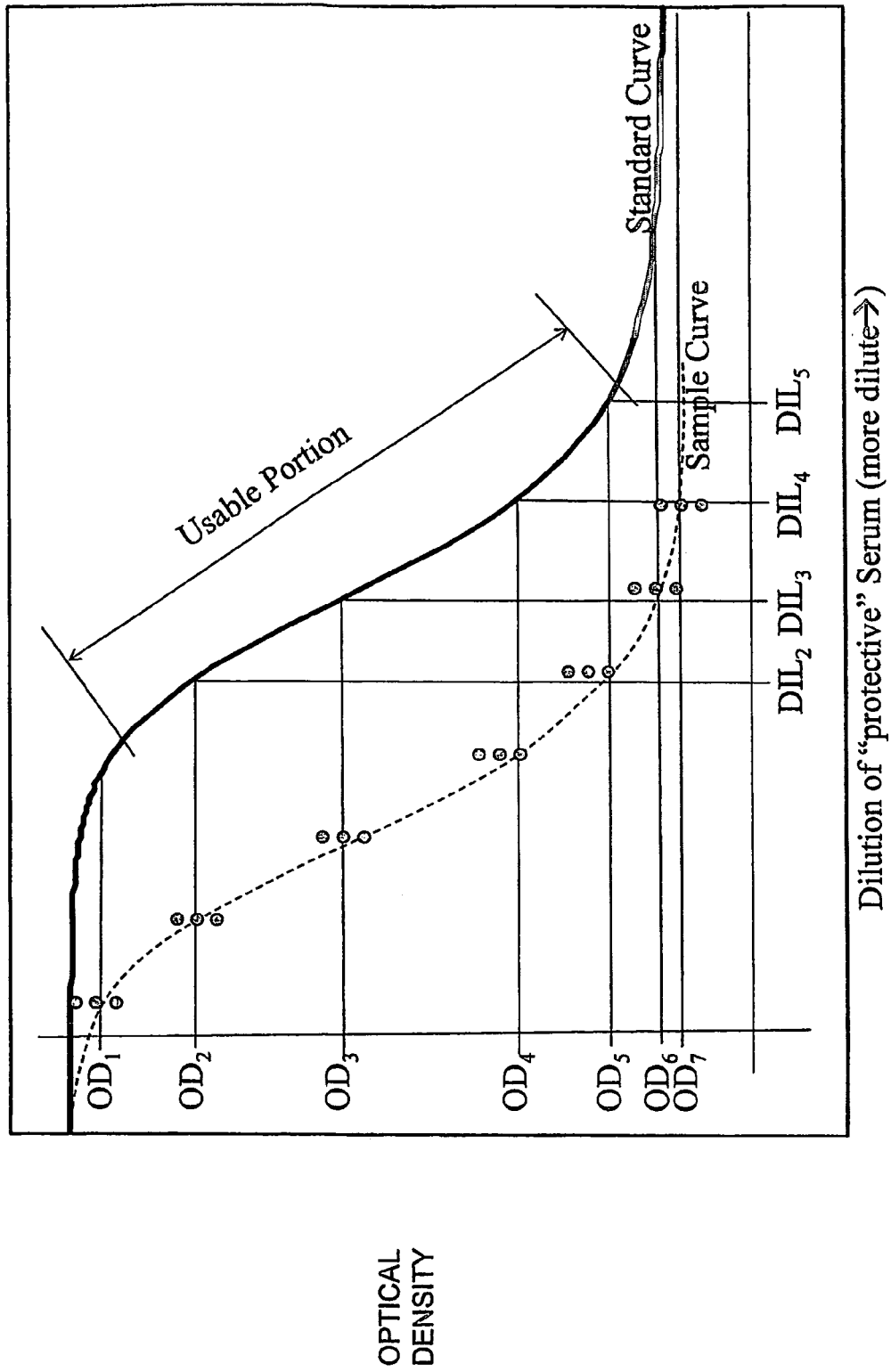
FIG. 10 shows an exemplary plot illustrating back-calculation of concentrations.
Figure 11:
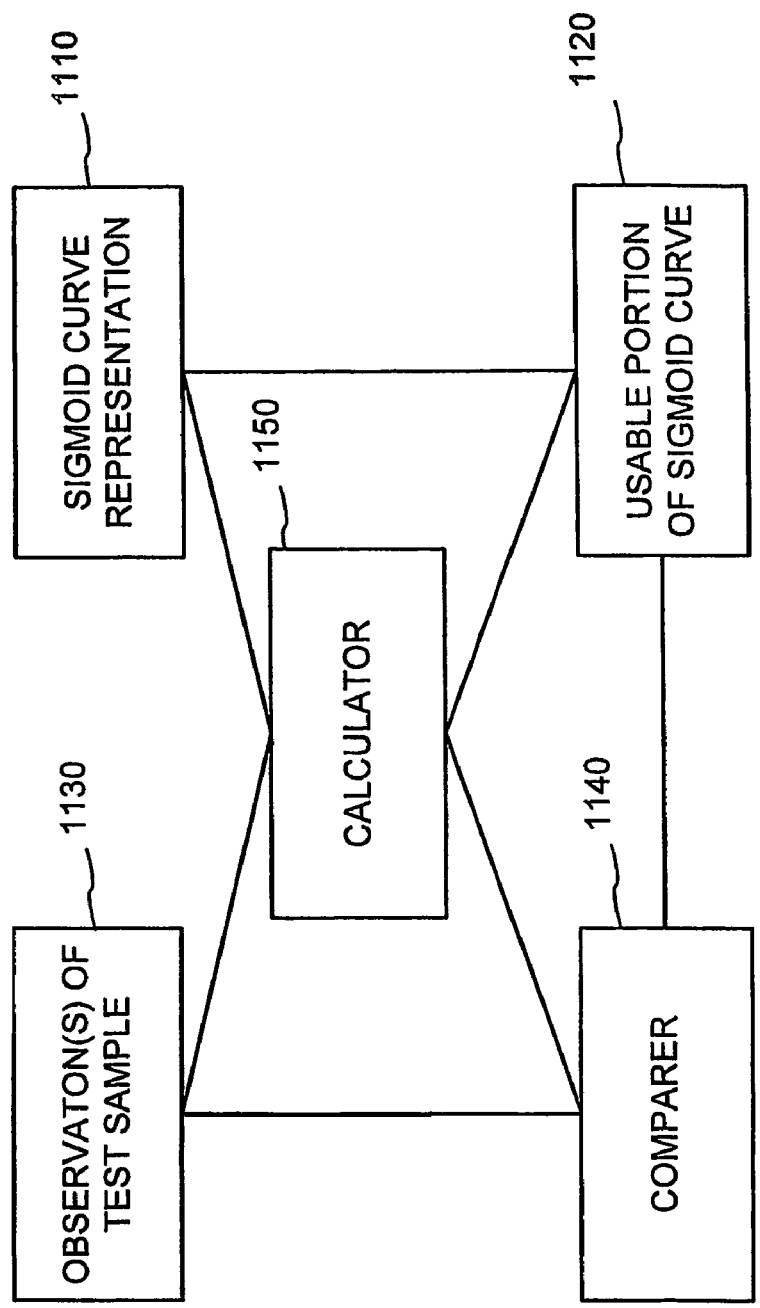
FIG. 11 is a block diagram showing an exemplary system for carrying out the technologies described herein.

FIG. 7 illustrates a back-calculation of concentration (e.g., use of the inverse of the four-parameter logistic function) via a standard sigmoid curve. In the example, concentration of anthrax anti-Protective Antigen (anti-PA) IgG is being calculated to determine the concentration or presence of anthrax. However, the technique can be applied to any number of other scenarios for calculating concentration of a substance.

In the example, a usable portion of the curve has been determined. For observations along the test-sample curve, concentrations are found. Certain observations (e.g., $OD_7$) have values not within the usable portion of the curve; therefore they are not used (e.g., are discarded). Thus, a subset of the observations (e.g., those associated with the usable portion of the standard curve) is used to calculate concentration.

EXAMPLE 7

Exemplary Modeling of Sigmoid Curve in Optical Density Scenarios

In any of the examples described herein, the sigmoid curve can represent observed optical density for a plurality of serial dilutions. For example, a reference sample having a known concentration of a substance can be observed by measuring the optical density of a plurality of observations for a plurality of dilutions of the sample. The sample can be subjected to various conditions before or after dilution.

In some scenarios, the dilution lessens the amount of protective (e.g., cell-saving or antibody) agent, resulting in increased cell death. Optical density measurements at an appropriate wavelength can be used to measure the number of living cells.

EXAMPLE 8

Exemplary Applications in Antibody Scenarios

In any of the examples described herein, the technologies can be applied to measure the concentration of antibody in a sample. For example, the sample can be diluted and added to a set of cells in the presence of a cell toxin. The presence of antibody will protect the cells from the toxin; the concentration of living cells thus indicates concentration of the antibody. Alternative techniques, such as measuring binding (e.g., via a label or other marker) can be used.

Presence of antibody can indicate presence of a toxin. For example, in one implementation, the concentration of anthrax is indirectly determined by measuring the presence of anti-PA IgG. When constructing a standard curve for such a scenario, dilution can reduce the amount of protective serum (e.g., a sample containing anti-PA IgG) that tends to preserve the life of cells. A low optical density thus indicates more dead cells; a high density indicates more living cells. Less protective serum tends to result in more dead cells and thus a lower optical density.

A sample having low optical density below the threshold titer is considered to test negative for anthrax (e.g., there was no anti-PA IgG to protect the cells). Various other procedures can be combined into a standard protocol to promote uniformity of results across test samples.

EXAMPLE 9

Exemplary Technique for Determining Concentration of Antibody

Any of the technologies described herein can be used to test for the concentration or presence of antibody. For example, a method for testing a blood serum sample for the concentration of antibody in the blood sample can proceed as follows:

(1) measuring the optical density of a test sample, wherein the test sample is generated by adding the serum to cells and a toxin neutralized by the antibody;

(2) determining whether a measurement indicating concentration of live cells (e.g., the optical density) falls within a usable portion of a standard sigmoid curve representing observations taken of a sample having a known concentration of antibody; and (3) responsive to determining the measurement indicating concentration of live cells (e.g., optical density) falls within the usable portion, calculating a concentration via the standard sigmoid curve.

In any of the examples, the antibody can be anti-PA IgG, which indicates infection by the anthrax toxin.

During the method, one or more observations having an optical density outside the usable portion of the standard sigmoid curve can be discarded. The usable portion of the sigmoid curve can be determined via a second derivative of the sigmoid curve as described in any of the examples.

EXAMPLE 10

Exemplary Applications

The technologies described herein can be used in conjunction with any dilution-range-type micro-biological assay, including but not limited to enzyme-linked immunosorbent assay ("ELISA"), toxin neutralization/neutralizing assay ("INA"), and flow opsono techniques.

The technologies described herein can be applied in a variety of other bioassay analysis scenarios to advantage. For example, the technologies can also be applied with advantage to polymerase chain reactive ("PCR") assay, radioimmuno assay ("RIA"), cell growth assay, cell death assay, and flow cytometry scenarios, or any test in which sample results are derived from a standard sigmoid curve.

EXAMPLE 11

Exemplary Observations

Observations can be taken in a variety of ways to determine concentration of a substance. For example, in biological scenarios, the number of living cells can be measured (e.g., by measuring optical density at an appropriate wavelength).

Alternatively, a binding agent can be used. Such a binding agent may include a marker (e.g., chemical, fluorescent, radioactive, and the like). The marker can assist in detection. After binding, an observation can be taken by measuring the resulting bound substance (e.g., by measuring optical density).

EXAMPLE 12

Exemplary Results

Serum samples were analyzed during 2001, 2002, and 2003 according to a protocol for a TNA for anti-PA antibodies. The protocol is described in Quinn et al., "Specific, sensitive, and quantitative enzyme-linked immunosorbent assay for human immunoglobulin G antibodies to anthrax toxin protective antigen", *Emerging Infectious Diseases,* 8:10, Centers for Disease Control, October 2002, (available at http://www.cdc.gov/ncidod/EID/vol8no10/02-0380.htm) which is hereby incorporated herein by reference. A standard human serum was tested for neutralization of PA toxin separately on 103 plates.

Four samples including a serum standard (AVR414) sample were analyzed on each plate. Each sample consisted of a seven-point dilution with triplicates at each dilution. For samples which met primary quality control ("QC"), four-parameter logistic curves (see Formula 1) were fitted to the raw data, using the NLIN procedure of SAS software (SAS Institute, Cary N.C., USA). FIG. 8 shows an exemplary curve 810 fit to data and the associated confidence bands 820A, 820B. From the fitted curves, for a standard human serum tested for neutralization of PA toxin separately on 103 plates, four titers were computed: effective-dose 50% ("ED50"), minimum detectable concentration ("MDC") and reliable detection limit ("RDL") from O'Connell, the threshold titer described herein, the quantification titer described herein, and antibody concentration.

The statistical observations and analytical conclusions are based on empirical data developed by Center for Disease Control's anthrax serology lab over the last two years. Numeric results apply specifically to subsets of approximately 1500 anthrax TNA plates which have been analyzed in the lab and whose lab results have been analyzed statistically.

Quantification Titer, and Threshold Titer involved less variability as measured by Coefficient of Variation ("CV") and by range of values over the 103 plates. The results are shown in Table 1. Titer indicates some measure of concentration. For the nominal lower limit, MDC ranged from 1600 to 11,650 with an overall CV of 41%, whereas the Threshold Titer ranged from 1690 to 8,810 with a CV of 37%. For the reliable lower limit, RDL ranged from 1180 to 7,660 with a CV of 38%, while the Quantification Titer ranged from 1130 to 3,960 with a CV of 29%.

TABLE 1

Comparison of MDC and RDL to TT and QT (n = 103)

| | MDC | TT | RDL | QT |
|---|---|---|---|---|
| Range | 1,600-11,650 | 1,690-8,810 | 1,180-7,660 | 1,130-3,960 |
| CV | 41% | 37% | 38% | 29% |

EXAMPLE 13

Exemplary Explanation

The described technologies can take advantage of the fact that the knees (i.e., the upper and lower bends) of a symmetric sigmoid curve (e.g., the four-parameter logistic-log curve) can be identified directly through the use of the first and/or second derivatives. Such an approach can be superior to the O'Connell approach, which evaluates error in the inverse function.

The described Quantification Titer and Threshold Titer are especially precise for assays whose curve-fit is especially good (e.g., curves whose R-squares [R-squared for the non-linear curve fit is defined as the difference between the sum of squares for the observed values and the sum of squares for the residuals divided by the sum of squares for the observed values: $(SSQ_{observed}-SSQ_{residual})/SSQ_{observed}$] are in the range of 0.99 to 1.00).

EXAMPLE 14

Exemplary ED50, Titers, and Concentration

In general, titers are computed by identifying some response threshold. Then, the fitted curve is used to translate that threshold from the response axis (y or vertical axis) to the dilution axis (x or horizontal axis). An example is shown in FIG. 9.

Methods of determining that response threshold are described herein. Also, the four-parameter logistic ("4PL") curve was used to "back-compute" (e.g., apply the inverse 4PL function to compute) sample concentrations, by applying the relationship between response variable (optical density) and dilution from the standard-serum curve to the observed sample curve or raw data points. An example is shown in FIG. 10.

EXAMPLE 15

Exemplary Combination of Technologies

The described technologies can be incorporated into a TNA system. The system can compute the 4PL curve, the ED50, two implicit titers (e.g., threshold and quantification), the usable portion of the curve or quantification range, and the implicit concentrations of test samples. The method system can identify the "knees" of the 4PL curve directly through the use of the derivatives.

The Threshold Titer can be defined using an empirically derived threshold in the first derivative to define the point on the curve, thereby identifying a titer point on the dilution scale (e.g., as shown in FIG. 5). The second-derivative characteristics of the curve further identify the knees by the relatively rapid change in slope. The domain between the knees is the quantification range of the curve. The Quantification Titer can be the dilution corresponding to the upper (lower dilution) end of the quantification range (e.g., as shown in FIG. 4)

EXAMPLE 16

Exemplary Information Regarding Using Sigmoid Curves to Calculate Concentration The fitted curve for the standard serum, having passed primary and secondary quality control ("QC"), can establish the normalized relationship between optical density ("OD") and dilution for a specific plate. Mathematically, this establishes OD as a function of dilution, i.e. OD=$f$(DIL), where $f$ is the four-parameter logistic function. This is called the standard curve or characteristic curve for the plate.

Further, the usable portion of the standard curve is that domain of dilutions or that corresponding range of OD's over which the inverse function can be used reliably, where "reliably" is defined by a specified level of precision, typically stated as a specified percent-CV across the implicit concentrations either across each and every dilution ("within-dilution") or across all dilutions ("within assay.") That is, the inverse function, DIL=$f^{-1}$(OD) can be and is applied to the OD's of the test samples to "back-calculate" the dilutions and therefore the initial sample concentrations, since the starting titration dilutions are known.

FIG. 7 shows an exemplary sigmoid curve employed in a back calculation technique. A possible procedure for use with the curve is: (1) fit the standard curve, pass QC tests, (2) define the usable portion of the curve, (3) for test OD's within the usable portion of the standard curve, back-calculate the dilutions, and (4) adjust the back-computed dilutions for the starting titration dilution to calculate the Anti-PA IgG concentrations of the test samples. Details vary according to study-specific protocols.

EXAMPLE 17

Exemplary Protocol

Any of the examples described herein can be used in any number of protocols. For example, a certain number of observations falling within the usable portion of the curve can be required, various quality assurance ("QA") tests can be required, etc.

EXAMPLE 18

Exemplary Metrics

In any of the examples herein, a number of metrics can be used to determine the concentration of a substance. Some of the examples use a metric of optical density, but the technologies described herein can be applied to other metrics.

EXAMPLE 19

Exemplary Indirect Measurement

In any of the examples herein, the technologies can measure the concentration of one substance to indicate the concentration of another substance. Thus, measurement of a concentration can be achieved indirectly. For example, for an antigen such as a toxin, the concentration of antibody present in a sample taken from a subject (e.g., a human patient) can indicate the concentration of the toxin in the subject's body, for example the concentration in a body fluid, such as blood, for example, blood serum. Further, the concentration of live cells in the presence of a toxin can indicate the presence of an antibody neutralizing the toxin. Thus, the concentration of live cells in a toxin neutralization assay can be used to indirectly indicate the concentration of the toxin.

EXAMPLE 20

Exemplary Approaches Using Sample Curve

For any of the technologies described herein, a plurality of points can be used to generate a test (e.g., for a sample) sigmoid curve (e.g., according to the 4PL formula). The sample curve can then be used to calculate concentration in light of a usable portion of a standard sigmoid curve (e.g., determined via any of the technologies described herein). Such an approach can be used instead of or in addition to using points to calculate concentration.

Although examples herein describe arrangements in which the usable portion of the standard curve is determined, an approach could alternatively or in addition determine the usable portion of a test curve.

When determining concentration in light of the two curves, calculations can proceed by considering a number of points on the test curve within the usable portion of the standard curve (e.g., using a particular point resolution).

Even though a curve can be generated from test points falling outside the usable portion of the standard curve, it may be desirable to require one or more test points to fall within the usable portion of the standard curve (e.g., for quality control purposes).

EXAMPLE 21

Exemplary Advantages

Various advantages can be gained by using the examples described herein. The examples described herein may benefit from zero or more of the following advantages.

When the described technology is used across plates, it establishes very specific quantitative characteristics of a given material such as a serum standard.

The described technology allows great flexibility in determining if and how a reagent fits the expected model and therefore provides more robust computation of endpoints.

The described technology provides a strong quality control test for known material or substance.

The described technology increases accuracy.

The described technology increases repeatability.

Given an assay which is sufficiently precise biologically, the described technology presented improves on the reproducibility and therefore the accuracy and precision of prior computational methods.

For example, when the described technologies relating to first and second derivatives are applied to an anthrax TNA scenario, the long-run effect is that the stability of the described technology is higher (e.g., as measured by higher variance) than O'Connell's MDC and RDL.

The described technology provides a continuous, as opposed to discreet, endpoint determination and is therefore more precise. For purposes of illustration, assume a compared % CV technique can only use only specific, observed dilutions of the test-sample for end-points (e.g., of the usable portion of the curve). In a worst-case example, if the true (but yet-unknown) usable portion of a curve covered the domain from a dilution of for example, 500 to 1500, and the dilution sequence for the test sample were 200, 400, 800, 1600 . . . then the compared % CV approach would fail at 400 and fail at 1600, leaving only the test triplicate at 800 for the back-calculation. By many protocols, use of a single triplicate would be insufficient, so in this specific example, there would be no reportable test result.

By contrast, the described technology can avoid the above outcome if the test-sample itself produced an acceptable sigmoid curve. In such a case, additional OD points on the test curve between dilutions of 500 and 799 and between 801 and 1500 can be imputed, using knowledge of the test curve gained from the dilutions 400, 1600 and beyond, even though these data are outside the usable portion of the standard curve. These additional points can be used to back-calculate additional concentrations and produce reportable results. These results rely in a predictable way on information gained from the test curve and from the standard curve without constraint to the two or three test dilutions points (one point in the above example) which might happen to fall in the usable domain of the standard curve.

The described technology can define the usable portion of the curve before the application of the curve to the test-sample results, rather than after the application of the inverse function. In a comparison technique, the measure of the usable portion of the standard curve is whether or not it did work as evidenced by post-use error, (i.e. % CV in the implicit test-sample concentrations). By contrast, the described technology can directly measures the slope of the curve and the second-derivative characteristics of that slope, thereby allowing direct identification of the knees of the curve and the domain between the knees. Thus, the usable portion of the curve can be defined. The described technology can exploit the characteristics of the standard curve itself, rather than implicit characteristics based on any particular test sample.

EXAMPLE 22

Exemplary Concentration Units

Although the described technologies can be used with any concentration units, exemplary units used in association with determining concentration include titers, grams/liter (e.g., micrograms/milliliter), or other measurements of concentration.

EXAMPLE 23

Exemplary Implementations in Software

Any of the methods described herein can be implemented in software. For any of the methods implemented in software, the depicted actions can be achieved via computer-executable instructions carrying out the depicted actions. Such instructions can be encoded on one or more computer-readable media (e.g., RAM, ROM, CD-ROM, DVD, hard disk, removable media, flash media, and the like).

When implemented in software, the various inputs to the methods (e.g., observations of a test sample) can be provided via a user interface or sent directly via test equipment to the computer system. The outputs can be provided via user interface, sent directly to output, or communicated via a network to another computer system, as desired.

EXAMPLE 24

Exemplary System

FIG. 11 shows a system 1100 for carrying out the technologies described herein. In the example, a sigmoid curve is represented by a representation 1110 (e.g., a data structure or set of variables or fields). The usable portion of the sigmoid curve is represented by a representation 1120 (e.g., a data structure or set of variables or fields). One or more observations of a test sample can be received and stored in the storage 1130 (e.g., a database, array, or other data structure).

A comparer 1140 is operable to determine whether an observation of 1130 is within the usable portion of the sigmoid curve as indicated by the representation 1120. For example, a function or other logic can make such a determination.

A calculator 1150 is operable to calculate a concentration for the test sample via the observations 1130 and the sigmoid curve representation 1110. The calculator 1150 can be configured so that calculation is performed responsive to determining that the observation is within the usable portion of the sigmoid curve. Observations determined to be outside the usable portion of the sigmoid curve can be rejected.

The usable portion of the sigmoid curve as represented by the representation 1120 can be calculated via a second derivative of the sigmoid curve as described in any of the examples herein. The system 1100 can further include means for calculating such usable portion (e.g., by determining endpoints).

The pictured system 1100 can be implemented in software stored on one or more computer-readable media and can be implemented in any number of computer languages.

EXAMPLE 25

Exemplary User Interface

FIG. 12 shows a screen shot of an exemplary user interface 1200 by which results of the technologies described herein can be presented (e.g., in a window 1230).

In the example, analysis has been performed for six (6) samples. The window 1230 indicates the sample identifier, a concentration of a substance within the sample, an indication of whether the substance was present in the sample, the number of observations for the sample, and the number of observations discarded (e.g., for falling outside of the usable portion of the standard sigmoid curve).

Additional, fewer, or different elements can be added to the user interface 1200. For example, a representation (e.g., file name or list of parameters) of the sigmoid curve can be presented. Also, other discarded observations (e.g., failing to meet QC) can be noted. The presence of the substance can be alternatively indicated (e.g., by color, flashing text, or icon). Similarly, the other results can be alternatively indicated.

EXAMPLE 26

Other Exemplary User Interfaces

Figure 13:
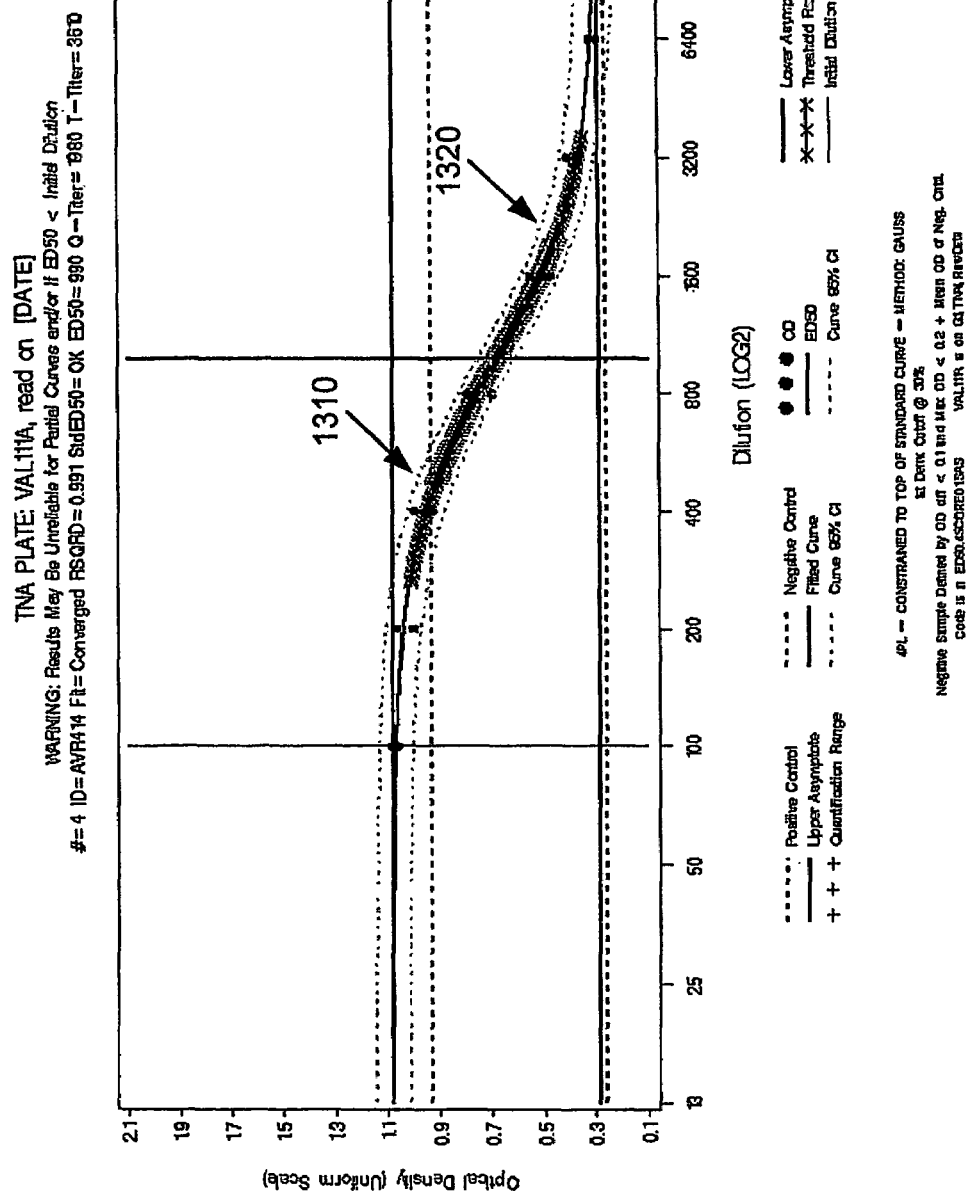
FIG. 13 is a screen shot of an exemplary user interface for presenting results of the technologies as applied to a standard sigmoid curve.

FIG. 13 shows a screen shot of an exemplary user interface 1300 for presenting results related to a standard curve. In the example, the usable portion of the curve between 1310 and 1320 is depicted in one color (e.g., blue), and the points outside the useable portion but within the thresholds are depicted in another color (e.g., brown). The remainder of the curve is in yet another color (e.g., black).

Figure 14:
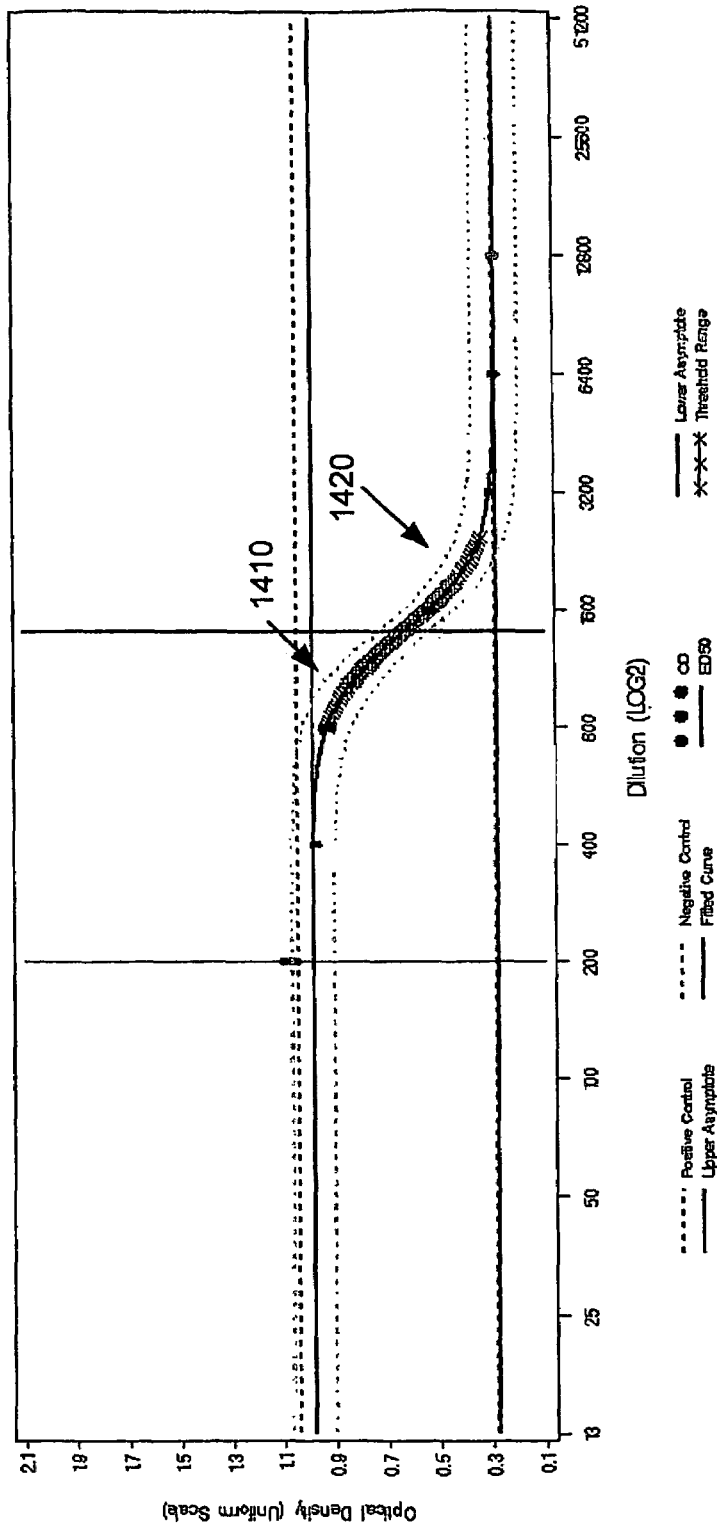
FIG. 14 is a screen shot of an exemplary user interface for presenting results of the technologies as applied to a test sigmoid curve.

FIG. 14 shows a screen shot of an exemplary user interface 1400 similar to that of FIG. 13, but for a test curve. Again, the usable portion of the curve between 1410 and 1420 can be depicted in one color (e.g., blue), and the points outside the usable portion but within the thresholds can be depicted in another color (e.g., brown). The remainder of the curve can be in yet another color (e.g., black).

FIGS. 15 and 16 show a screen shot of an exemplary user interface 1500, 1600 that presents results in text form. The interface includes both point-based IgG concentration (e.g., determined applying actual observations to a standard sigmoid curve) and curve-based IgG concentration (e.g., determined applying a curve fit to actual observations to a standard sigmoid curve).

Any combination of the user interface described herein can be used in software. Additional, fewer, or different elements can be used as an alternative to those pictured.

EXAMPLE 27

Exemplary Alternatives

For those actions specified as computer-executable, such actions can be performed fully-automatically (e.g., without human intervention) or semi-automatically (e.g., with assistance from a human operator). One or more computer-readable media can comprise the instructions described as computer-executable.

Various implementations of the technologies described herein can be called the "Taylor method," named after inventor Thomas H. Taylor, Jr.

In view of the many possible embodiments to which the principles of the invention may be applied, it should be recognized that the illustrated embodiments are examples of the invention, and should not be taken as a limitation on the scope of the invention. Rather, the scope of the invention includes what is covered by the following claims. I therefore claim as my invention all that comes within the scope and spirit of these claims.

I claim:

1. One or more computer-readable media comprising computer-executable instructions for performing a method to calculate concentration of a substance in a test sample, the method comprising:

after a second derivative is calculated for a standard sigmoid curve, finding a first point on the standard sigmoid curve via the second derivative of the standard sigmoid curve and designating the first point as a first bound;

finding a second point on the standard sigmoid curve via the second derivative of the standard sigmoid curve and designating the second point as a second bound;

determining a usable portion of the standard sigmoid curve as a plurality of points on the standard sigmoid curve between the first bound and the second bound;

for at least one observation of a metric for the test sample, determining whether the at least one observation is within the usable portion of the standard sigmoid curve; and responsive to determining that the at least one observation is within the usable portion, calculating a concentration of the substance based on a location of the observation on the standard sigmoid curve.

2. The one or more computer-readable media of claim 1 wherein the standard sigmoid curve is represented via a four-parameter formula.

3. The one or more computer-readable media of claim 1 wherein the standard sigmoid curve represents a sigmoid curve fit to a plurality of observations taken of a reference sample having a known concentration of the substance.

4. The one or more computer-readable media of claim 1 further comprising computer-executable instructions for performing the following:

determining for at least one observation of a metric for the test sample whether the observation is above a threshold value, wherein the threshold value is determined via a first derivative of the standard sigmoid curve; and indicating whether the observation is above the threshold value.

5. The one or more computer-readable media of claim 1 wherein:

the observation indicates optical density for the test sample.

6. The one or more computer-readable media of claim 5 wherein:

the concentration indicates an amount of antibody in the test sample.

7. The one or more computer-readable media of claim 6 wherein:

the concentration indicates an amount of anti-PA IgG in the test sample.

8. The one or more computer-readable media of claim 1 wherein the finding of the first point and the second point on the standard sigmoid curve is performed using a local maximum of the second derivative, a local minimum of the second derivative, an inflection point of the second derivative, or a combination thereof.

9. The one or more computer-readable media of claim 1 wherein the first point corresponds to a local maximum of the second derivative and the second point corresponds to a local minimum of the second derivative.

10. The one or more computer-readable media of claim 1 wherein the method further comprises:

when the at least one observation is not within the usable portion, indicating that the at least one observation is not used in the calculating of the concentration of the substance.

11. The one or more computer-readable media of claim 1 wherein:

the usable portion corresponds to a range of measurement values; and the determining of whether the observation is within the usable portion of the standard sigmoid curve comprises determining whether a measurement value associated with the at least one observation is within the range of measurement values.

12. One or more computer-readable media comprising computer-executable instructions for performing a method to calculate concentration of a substance in a test sample, the method comprising:
- for a plurality of observations of a metric for the test sample, fitting a test sigmoid curve to the observations;
- determining a usable portion of a standard curve, wherein the determining comprises performing (a)-(c):
- (a) finding a first endpoint of the usable portion via a second derivative of the standard curve;
- (b) finding a second endpoint of the usable portion via the second derivative of the standard curve; and
- (c) determining the usable portion of the standard curve as a portion of the standard curve between the first endpoint and the second endpoint;
- discarding one or more of the observations that are outside the usable portion of the standard curve; and
- calculating a concentration of the substance in the test sample via the test sigmoid curve and the usable portion of the standard curve.

13. The one or more computer-readable media of claim 12 further comprising computer-executable instructions for performing the following:
- indicating the concentration of the substance.

14. The one or more computer-readable media of claim 12 further comprising computer-executable instructions for performing the following:
- displaying the concentration of the substance.

15. The one or more computer-readable media of claim 12 wherein the method further comprises:
- selecting from the plurality of observations a subset of observations that falls within the usable portion of the standard curve, wherein the calculating of the concentration is performed using the subset of observations and the usable portion of the standard curve.

16. One or more computer-readable media comprising computer-executable instructions for performing a method to calculate concentration of a substance in a test sample, the method comprising:
- finding a usable portion of a sigmoid curve, wherein the finding comprises calculating a second derivative of the sigmoid curve and finding a first point and a second point on the sigmoid curve using the second derivative, wherein the usable portion of the sigmoid curve comprises a plurality of points on the sigmoid curve between the first point and the second point; and
- calculating a concentration of the substance in the test sample via the usable portion of the sigmoid curve.

17. One or more computer-readable media comprising computer-executable instructions for performing a method comprising:
- for a plurality of dilutions of a test sample, receiving respective measurements of optical density indicating concentration of live cells within the dilutions;
- designating a first point and a second point on a sigmoid curve using a second derivative of the sigmoid curve;
- defining a plurality of points on the sigmoid curve between the first point and the second point as a usable portion of the sigmoid curve;
- discarding one or more of the measurements that are outside the usable portion of the sigmoid curve;
- via the remaining measurements, calculating a concentration of anti-PA IgG for the test sample via the usable portion of a sigmoid curve representing concentrations of live cells within dilutions of a reference sample having a known quantity of anti-PA IgG, wherein the sigmoid curve is represented via a four-parameter logistic technique; and
- indicating the concentration of anti-PA IgG for the test sample.

18. A computer-implemented method of calculating concentration of a substance in a test sample having an unknown concentration of the substance, the method comprising:
- determining a usable portion of a sigmoid curve fit to data points representing observations of a reference sample having a known concentration of the substance by calculating second derivative values for the sigmoid curve and selecting a first point and a second point on the sigmoid curve using the second derivative values, wherein the usable portion of the sigmoid curve comprises a range of a plurality of points between the first point and the second point;
- based on the usable portion of the sigmoid curve, selecting from a plurality of observations of the test sample, a subset of observations of the test sample within the usable portion of the sigmoid curve; and
- calculating the concentration of the substance in the test sample based on the subset of observations of the test sample.

19. The method of claim 18 further comprising:
- excluding at least one of the plurality of observations of the test sample responsive to determining the at least one of the plurality of observations is outside the usable portion of the sigmoid curve.

20. The method of claim 18 wherein the first point and the second point correspond to a minimum and a maximum of the second derivative values.

21. The method of claim 18 wherein a third point on the sigmoid curve relating to a threshold for a first derivative of the sigmoid curve is used as a lower threshold to indicate presence of the substance.

22. A computer-implemented method of determining the concentration of antibody in a blood serum sample, the method comprising:
- receiving a measurement indicative of concentration of live cells in a test sample, wherein the test sample is generated by adding the serum to cells and a toxin neutralized by the antibody;
- determining a usable portion of a standard sigmoid curve representing observations taken of a sample having a known concentration of antibody, wherein the determining comprises performing (a)-(c):
- (a) calculating second derivative values for the standard sigmoid curve;
- (b) selecting a first point and a second point on the standard sigmoid curve using the second derivative values; and
- (c) determining the usable portion of the standard sigmoid curve as a plurality of points on the standard sigmoid curve between the first point and the second point;
- determining whether the measurement falls within the usable portion of the standard sigmoid curve; and
- when the measurement falls within the usable portion, calculating a concentration via the measurement and the usable portion of the standard sigmoid curve.

23. The method of claim 22 wherein results for plural test samples for plural dilutions of an original test sample are included in the calculating.

24. The method of claim 22 wherein concentration of live cells is indicated by optical density of the test sample.

25. The method of claim 22 wherein the antibody is anti-PA IgG.

26. The method of claim 22 further comprising:
discarding the measurement when the measurement is outside the usable portion of the standard sigmoid curve.

27. One or more computer-readable media having computer-executable instructions for performing a method of determining the concentration of antibody in a blood serum sample, the method comprising:
receiving a measurement indicative of concentration of live cells in a test sample, wherein the test sample is generated by adding the serum to cells and a toxin neutralized by the antibody;
determining a usable portion of a standard sigmoid curve representing observations taken of a sample having a known concentration of antibody, wherein the determining comprises performing (a)-(c):
(a) calculating second derivative values for the standard sigmoid curve;
(b) selecting a first point and a second point on the standard sigmoid curve using the second derivative values; and
(c) determining the usable portion of the standard sigmoid curve as a plurality of points on the standard sigmoid curve between the first point and the second point;
determining whether the measurement falls within the usable portion of the standard sigmoid curve; and
when the measurement falls within the usable portion, calculating a concentration via the measurement and the usable portion of the standard sigmoid curve.

28. A software system encoded on one or more computer-readable media, the software system comprising:
a representation of a characteristic sigmoid curve;
means for designating a usable portion of the characteristic sigmoid curve by calculating a second derivative for the characteristic sigmoid curve and selecting a first point and a second point on the characteristic sigmoid curve using the second derivative, wherein the usable portion comprises a range of a plurality of points between the first point and the second point;
means for receiving at least one observation of a test sample;
means for determining whether the observation of the test sample is within the usable portion of the characteristic sigmoid curve; and
means for calculating a concentration for the observation responsive to determining that the observation is within the usable portion of the characteristic sigmoid curve.

29. The software system of claim 28 further comprising:
means for rejecting an observation responsive to determining that the observation is outside the usable portion of the characteristic sigmoid curve.

30. One or more computer-readable media comprising computer-executable instructions for performing a method to indicate presence of a substance in a test sample, the method comprising:
for at least one observation of a metric for the test sample, determining whether the observation is higher than a threshold value, wherein the threshold value is determined via a first derivative of a standard sigmoid curve;
responsive to determining the observation is higher than the threshold value, indicating presence of the substance;
calculating a second derivative of the standard sigmoid curve;
selecting a first point and a second point on the standard sigmoid curve using the second derivative;
defining a plurality of points on the standard sigmoid curve between the first point and the second point as a usable portion of the standard sigmoid curve; and
calculating a concentration of the substance in the test sample when the at least one observation falls within the usable portion of the standard sigmoid curve.

* * * * *